US00PP10498P

United States Patent [19]

Verwer

[11] Patent Number: Plant 10,498

[45] Date of Patent: Jul. 14, 1998

[54] DAHLIA PLANT NAMED 'GALLERY LEONARDO'

[75] Inventor: Aad Verwer, Lisse, Netherlands

[73] Assignee: Gebr, Verwer, Lisse, Netherlands

[21] Appl. No.: 815,865

[22] Filed: Mar. 12, 1997

[51] Int. Cl.[6] ..... A01H 5/00

[52] U.S. Cl. ..... Plt./87.8

[58] Field of Search ..... Plt./87.8

[56] References Cited

U.S. PATENT DOCUMENTS

P.P. 899 11/1949 Gilmore ..... Plt./87.8

OTHER PUBLICATIONS

GTITM Upovrom Listing for 'Gallery Leonardo' as per PBR Dhloo66 (NL) Mar. 16, 1996.

*Primary Examiner*—James R. Feyrer
*Assistant Examiner*—Kent L. Bell
*Attorney, Agent, or Firm*—C. A. Whealy

[57] ABSTRACT

A distinct cultivar of Dahlia plant named 'Gallery Leonardo', characterized by its suitability for potted plants, garden or patio plants, or as cut flowers; upright and spreading, compact and freely branching plant habit; dark green foliage; early and profuse flowering; rapid growth rate; large decorative-type inflorescences that are about 11 cm in diameter; salmon-colored ray florets; and good post-production longevity.

1 Drawing Sheet

The present invention relates to a new and distinct cultivar of Dahlia plant, botanically known as Dahlia hybrid and referred to by the cultivar name 'Gallery Leonardo'.

The new cultivar was discovered by the inventor in a controlled environment in Lisse, The Netherlands, in 1992, as a naturally-occurring mutation of the nonpatented Dahlia cultivar 'Decorette'. The new cultivar was observed as a single plant in a group of 13-cm flowering plants of the parent cultivar. The selection of this plant was based on its unique ray floret color.

Asexual reproduction of the new cultivar by terminal cuttings taken in a controlled environment in Lisse, The Netherlands, has shown that the unique features of this new Dahlia are stable and reproduced true to type in successive generations.

The cultivar 'Gallery Leonardo' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gallery Leonardo'. These characteristics in combination distinguish 'Gallery Leonardo' as a new and distinct cultivar:

1. Suitable for potted plants, garden or patio plants, or as cut flowers.
2. Upright and spreading, compact and freely branching plant habit.
3. Dark green foliage.
4. Early and profuse flowering.
5. Rapid growth rate.
6. Large decorative-type inflorescences that are about 11 cm in diameter.
7. Salmon-colored ray florets.
8. Good postproduction longevity with open inflorescences maintaining good substance and color for least 10 days and plants maintaining good substance and flowering for 3 to 4 months.

The accompanying photograph illustrates the overall appearance of the new cultivar. The colored photograph comprises a side perspective view of a typical flowering plant of 'Gallery Leonardo'. This photograph shows the colors as true as it is reasonably possible to obtain in colored reproductions of this type. Floret and foliage colors in the photograph may differ from the actual colors due to light reflectance.

In the following description, color references are made to The Royal Horticultural Society Colour Chart except where general terms of ordinary dictionary significance are used. The following observations and measurements describe plants grown in Lisse, The Netherlands, under conditions which approximate those generally used in commercial potted Dahlia production with day temperatures averaging 21° C. and night temperatures averaging 14° C. Plants are grown during the summer and measurements and numerical values were averages derived from typical flowering plants in September.

Botanical Classification: Dahlia hybrid cultivar 'Gallery Leonardo'.

Commercial classification: Decorative potted Dahlia.

Parentage: Naturally-occurring mutation of Dahlia hybrid cultivar 'Decorette' (not patented).

Propagation:

*Type.*—Terminal tip cuttings or by tuberous divisions.

*Time to rooting.*—About 14 days with soil temperatures of 20° C.

*Rooting habit.*—Central root with numerous secondary roots that are fine and fibrous.

Plant description:

*Appearance.*—Perennial herbaceous decorative-type Dahlia, suitable as potted plants, garden or patio plants, or as cut flowers. Upright and spreading, compact habit and freely branching.

*Plant height.*—About 25 cm, appropriate for 12 to 15-cm containers.

*Growth rate.*—Rapid, typically only 55 to 60 days are required from an unrooted cutting to a finished flowering plant.

*Foliage description.*—Leaf arrangement: Opposite, simple or compound. Compound leaves have either three or five leaflets. Leaf size, single: Length: About 6 cm. Width: About 4 cm. Leaf size, compound: Length: About 16 cm. Width: About 11 cm. Leaf shape: Elliptic to ovate. Leaf apex: Acute. Leaf base: Acute. Leaf margin: Serrate. Leaf texture: Smooth. Color: Young foliage adaxial surface: 144B. Young foliage abaxial surface: 147D. Mature foliage adaxial surface: 147A, occasionally with anthocyanin at margins. Mature foliage abaxial surface:

148D. Venation adaxial surface: 147A. Venation abaxial surface: 145A with anthocyanin. Petiole: Length: About 4 cm. Color: 145A with anthocyanin.

Inflorescence description:

*Appearance.*—Fully double decorative-type inflorescence form with salmon-colored ray florets. Inflorescences borne on terminals above foliage.

*Flowering response.*—Under natural conditions, plant flower from July to November in the Northern Hemisphere.

*Postproduction longevity.*—On the plant, open inflorescences will maintain good color and substance for at least 10 days. As a cut flower, open inflorescences will maintain good color and substance for at least 5 days. Plants will continue to maintain good substance and flowering for three to four months.

*Quantity of inflorescences.*—Numerous, continuous flowering.

*Inflorescence size.*—Diameter: About 11 cm. Depth (height): About 1.5 cm.

*Inflorescence bud.*—Size: Length: About 8 mm. Width: About 1.3 cm. Rate of opening: About 14 days. Color: 151C.

*Ray florets.*—Shape: Ovate. Size: Length: About 4 cm. Width: About 1.1 cm. Apex: Slightly curved and pointed. Margin: Entire. Texture: Smooth, shiny. Aspect: Curved downward. Color: When opening: 39A. Adaxial surface: 39A with 2A at base. Abaxial surface: 39B with 2B at base.

*Disc florets.*—Few and inconspicuous.

*Peduncle.*—Length: 6 to 17 cm. Aspect: Strong, erect. Texture: Glabrous. Color: 137C with anthocyanin.

*Sepals.*—Quantity: 5. Shape: Short and wide with pointed apex. Color: Adaxial surface: 144A with anthocyanin. Abaxial surface: 144B, venation and margin with anthocyanin.

*Reproductive organs.*—Androecium: Anther shape: Long and pointed. Anther length: Less than 1 mm. Anther color: 17B. Pollen color: 17A. Gynoecium: Stigma color: 16A. Style length: About 2 mm. Style color: 150B.

Disease resistance: No known Dahlia diseases observed to date on plants grown under commercial conditions.

Seed production: Seed production has not been observed.

It is claimed:

1. A new and distinct cultivar of Dahlia named 'Gallery Leonardo', as illustrated and described.

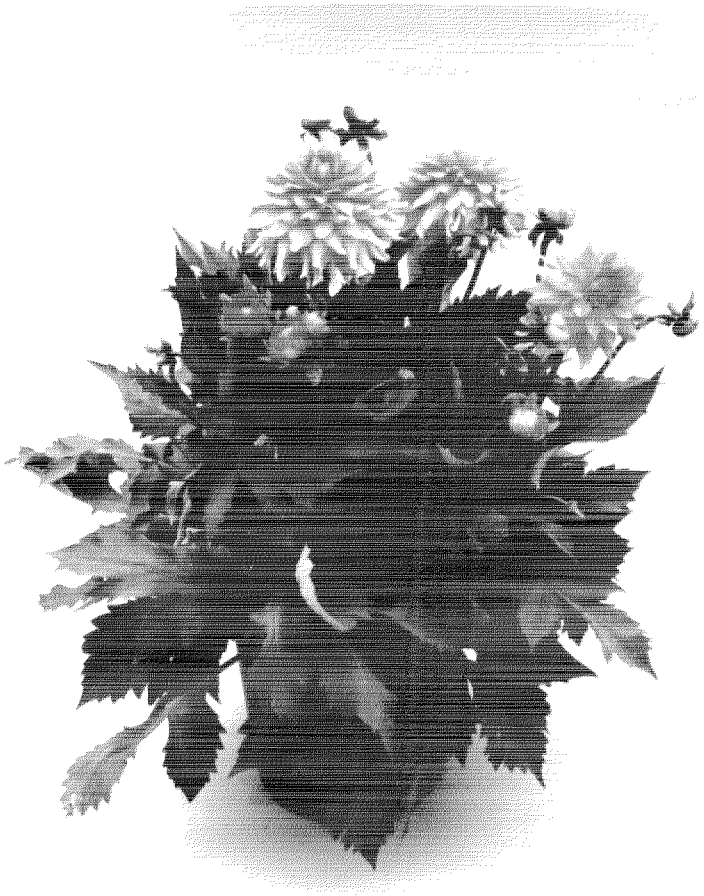

* * * * *